United States Patent
Jansson et al.

(10) Patent No.: US 6,607,701 B1
(45) Date of Patent: Aug. 19, 2003

(54) PRODUCTION OF MICROCUVETTES

(75) Inventors: Lars Jansson, Ängelholm (SE); Per Olsson, Munka Ljungby (SE); Norbert Pogorzelski, Helsingborg (SE); Ingrid Hultgren, Rydebäck (SE)

(73) Assignee: Hemocue AB, Ängelholm (SE)

( * ) Notice: Subject to any disclaimer, the term of this patent is extended or adjusted under 35 U.S.C. 154(b) by 0 days.

(21) Appl. No.: 09/541,894

(22) Filed: Apr. 3, 2000

Related U.S. Application Data

(63) Continuation of application No. PCT/SE98/01776, filed on Oct. 2, 1998.

(30) Foreign Application Priority Data

Oct. 3, 1997 (SE) ................................................ 9703624

(51) Int. Cl.$^7$ ................................................ B01L 3/00
(52) U.S. Cl. .................................... 422/102; 356/246
(58) Field of Search .............................. 422/100, 102; 356/246

(56) References Cited

U.S. PATENT DOCUMENTS

| | | | |
|---|---|---|---|
| 3,620,676 A | * | 11/1971 | Davis |
| 3,698,822 A | | 10/1972 | Polanyi |
| 4,088,448 A | | 5/1978 | Lilja et al. |
| 4,792,373 A | | 12/1988 | Hsei et al. |
| 5,300,779 A | * | 4/1994 | Hillman et al. ............. 250/341 |
| 5,472,671 A | * | 12/1995 | Nilsson et al. ............. 422/102 |
| 5,674,457 A | | 10/1997 | Williamsson et al. |
| 5,858,194 A | * | 1/1999 | Bell |
| 6,001,307 A | * | 12/1999 | Naka et al. .................... 422/81 |

FOREIGN PATENT DOCUMENTS

EP 0172540 A2 2/1986

* cited by examiner

Primary Examiner—Jeffrey Snay
(74) Attorney, Agent, or Firm—Burns, Doane, Swecker & Mathis, L.L.P.

(57) ABSTRACT

The invention concerns a method for continuous production of disposable capillary plastic microcuvettes including the steps of providing a first and a second sheet; providing at least one depression having a predetermined depth at a predetermined place in at least one of the sheets; introducing at least one additive or reagent in at least one depression; joining the first sheet and the second sheet for obtaining a body member including at least one cavity, the inner walls of which are defined by the at least one depression and a predetermined area of the opposite sheet and cutting out microcuvettes including at least one cavity and having a predetermined size and configuration from the body member, in such a way that at least one cavity of the microcuvette is communicating with the exterior atmosphere of the microcuvette through a capillary sample inlet opening. The invention also concerns a cuvette prepared according to the new method.

12 Claims, 1 Drawing Sheet

PRODUCTION OF MICROCUVETTES

This is a continuation of International Application No. PCT/SE98/01776, filed Oct. 2, 1998, that designates the United States of America and which claims priority from Swedish Application No. 9703624-8, filed Oct. 3, 1997.

The present invention concerns a new method for producing disposable microcuvettes or microdevices.

A microcuvette for sampling a fluid, mixing the sample with a reagent and directly making optical analyses of the sample mixed with the reagent is previously known from U.S. Pat. No. 4,088,448. This cuvette comprises a body member including two planar surfaces defining an optical path and placed at a predetermined distance from one another to determine the optical path length and to define a cavity having an inlet communicating said cavity with the exterior of the body member.

The cavity has a predetermined fixed volume, and the predetermined distance is chosen so as to permit the sample to enter the cavity by capillary force. Furthermore, a reagent is applied on the cavity surface.

This known cuvette has several advantages when compared with the conventionally used devices. It permits sampling of a liquid, mixing and chemically reacting it with a suitable reagent for e.g. colour development in the same vessel as the one used for the subsequent measurement. The cuvette disclosed in U.S. Pat. No. 4,088,448 thus simplifies the sampling procedure, reduces the number of utensils and, depending on the type of analysis, considerably improves the exactitude of the analysis by making the analysing procedure independent of the operating technique of the operator making the analysis.

At present microcuvettes based on the microcuvette disclosed in U.S. Pat. Nos. 4,088,488 and 5,674,457 are marketed for analysing e.g. hemoglobin and glucose. The accuracy and precision in the currently used cuvette production is excellent. An obvious disadvantage is that each cuvette has to be moulded in one piece and a specific tool is required for every type of cavity. Another disadvantage is the comparatively short stability due to the decomposition of the reagent mixture in e.g. the glucose cuvettes. The instability originates from the fact that different components of the reagents cannot be physically separated during the storage as, during the manufacture, the reagents are incorporated into the cuvette as a solution, which is subsequently dried. The dried reagent layer formed in the cuvette cavity therefore includes an intimate mixture of different reagent components. Furthermore, the design, particularly the depths of cuvettes having more than one cavity, cannot be selected at will and in view of the specific requirements for the specific analytical determination, but is restricted by the manufacturing method. For instance it is not possible to produce a cuvette having two cavities with different depths, of which the deepest cavity is most remote from the inlet opening by the current cuvette manufacturing technique.

In view of these problems with the presently used cuvettes and the manufacturing thereof a new manufacturing method, which satisfies the following conditions, is desired. The new manufacturing method should fulfil the following requirements:

It should make it possible to separate reagents, which would give the cuvette a prolonged stability.

It should be possible to effectively control the reagent distribution and separation of reagent components on the surface of the cavity.

It should permit a high flexibility in the choice of the cavity design.

It should permit the production of microcuvettes for photometric analysis with both high accuracy and precision.

It should permit the production of microcuvettes, wherein a deeper cavity is provided more remote from the sample inlet opening than a more shallow, capillary inlet cavity. The deeper cavity could be capillary or non-capilllary. When capillary, the deeper cavity is less capillary than the capillary inlet cavity.

It should permit continuous, high capacity production.

It should permit a modular production system, where the modules could be replaced or easily modified for a particular application.

It has now been found that these conditions can be satisfied by using the new manufacturing method according to the present invention.

Figure 1:
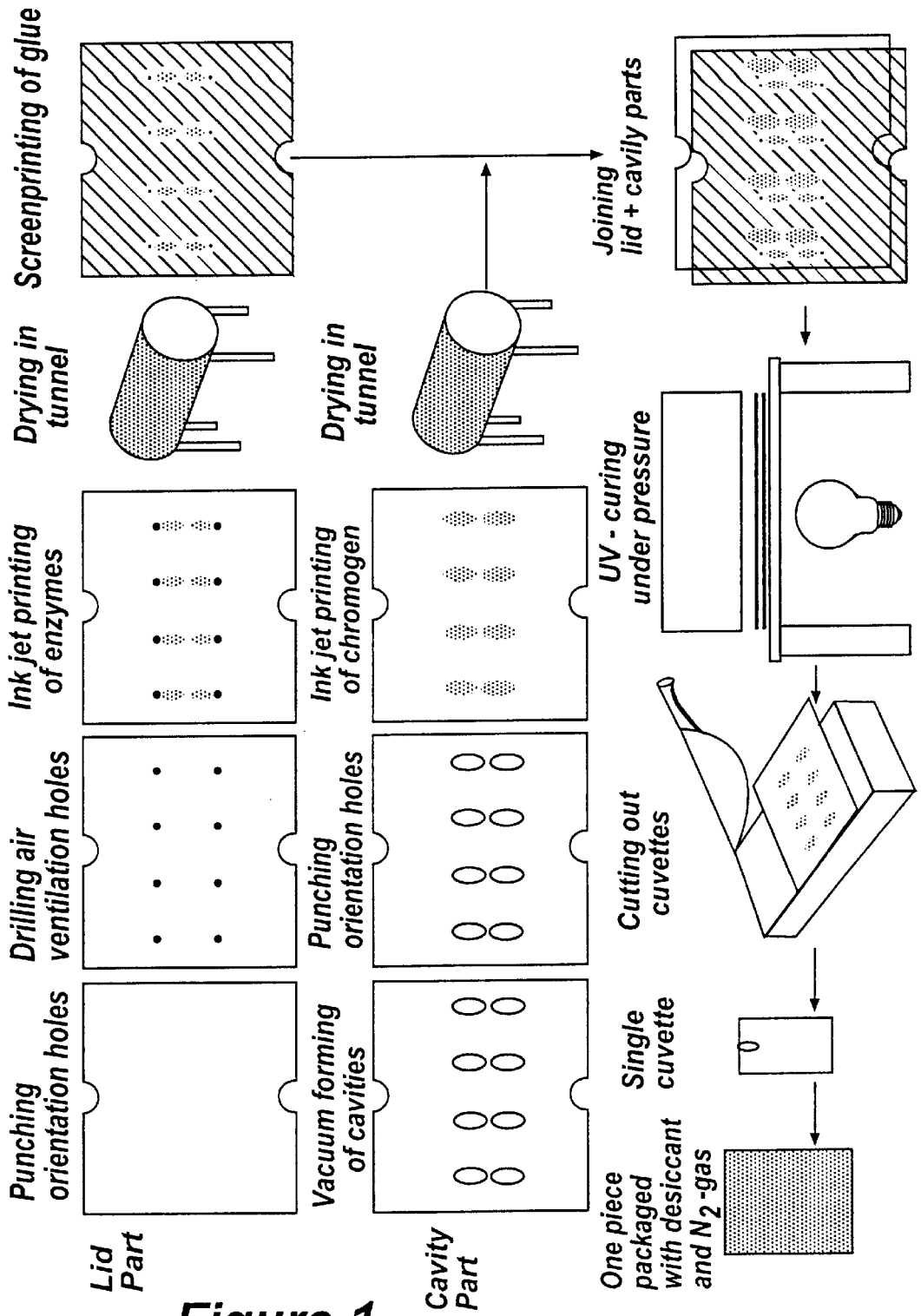
FIG. 1 depicts a method for production of disposable capillary plastic microcuvettes according to the invention.

In brief, this manufacturing method concerns the production of disposable capillary microcuvettes or microdevices, comprising the steps of providing a first and a second sheet;

providing at least one depression having a predetermined depth at a predetermined place in at least one of the sheets;

introducing at least one additive and/or reagent into at least one depression;

placing the sheets in a superimposed relationship;

joining the first sheet and the second sheet for obtaining a body member including at least one capillary cavity having a predetermined volume, the inner walls of the cavity being defined by the at least one depression and a predetermined area of the opposite sheet, the distance between these inner walls defining a predetermined optical path length, cutting out microcuvettes including at least one cavity and having a predetermined size and configuration from the body member, in such a way that at least one cavity of the microcuvette is communicating with the exterior atmosphere of the microcuvette through a capillary sample inlet opening. The inlet opening is preferably formed by this cutting.

According to this method, a new disposable capillary plastic microcuvette or microdevice for sampling a liquid, mixing the sample with reagents and directly making analyses of the sample mixed with the reagents is obtained. This microcuvette comprises a capillary sample inlet opening and at least one cavity including at least one dry reagent and/or additive. The cavity communicates with the exterior atmosphere of the microcuvette through the capillary inlet opening, through which the sample, e.g. whole blood, is drawn by capillary action. Furthermore, the new microcuvette is distinctive in that it is made up by two joined sheets, in at least one of which is provided at least one depression at a predetermined place and having a predetermined depth. The place and orientation of the depressions are not critical. Preferably the depressions are provided in such a way that each depression is surrounded by the sheet material. The alternative in which the depression is provided at the edge of the sheet is however also within the scope of the invention. In this alternative the capillary inlet opening is formed by the edge of the joined sheets.

A most important feature of the invention is based on the discovery that a very accurate predetermined depth suitable for very precise optical measurements can be produced using the vacuum forming or stamping technique, the vacuum forming technique being preferred as in this case a positive die is used and the surface facing the capillary cavity is not affected by the die. An additional advantage with a positive die is that it is independent of the thickness of the film material, which allows cavity formation with a very high precision.

The inner walls of the cavity are formed by the depression and a predetermined area of the inner surface of the adjoining sheet.

Optionally, holes are provided in at least one sheet. These holes are arranged in such a way that they form a vent hole in the final microcuvette.

Preferably the cavity has a predetermined volume. The inner surfaces of the walls defining the cavity are preferably essentially plane-parallel and define an optical path length or volume according to Beer's law.

The cavity includes a least one dried reagent and/or additive. If the reagent is made up by more than one substance, the different substances may be separated from each other in the same cavity by using e.g. a printing technique, such as ink jet printing or screen printing. The reagent, which is chosen depending on the analysis to be performed, is preferably introduced in the form of a solution which is subsequently dried e.g. by hot air.

The sheets, at least one of which is provided in the form of a continuous film, are preferably made of one and the same polymer material which should be thermoplastic and transparent. It is also preferred that the polymer is self-supporting. Examples of suitable polymer materials are PVC, PET, polystyrenes and polycarbonates.

The depressions are preferably obtained by vacuum forming or stamping. It is also preferred that a plurality of depressions be provided in one of the sheets and that the other sheet be planar. In this case each cavity is formed by a planar cover or lid and the depression.

Before joining the sheets, a reagent and/or additive, such as a surface modifying agent, may be provided in one or more depressions.

The surfaces of the sheets to be matched are then provided with an UV-sensitive adhesive, such as Loctite 3106 for PVC and Loctite 3108 for polycarbonate materials, which does not require a solvent that may damage the polymer material and which cures when irradiated with UV-light. Preferably the adhesive is applied by screen printing. When the surfaces have been pressed together the adhesive is cured by radiation, such as UV radiation. Other methods of joining the sheets, such as ultrasound welding, have turned out to be less attractive due to problems of obtaining accurate and reproducible cavity depths, i.e. optical paths. According to an embodiment of the invention the inner surfaces of the sheets, i.e. the surfaces facing the cavities, are provided with embossments determining the depth of the capillary cavity and guiding optional superfluous adhesive to areas between the embossments in such a way the adhesive does not have any impact on the cavity depth. Since in the production of microcuvettes, the cavity depth is very small, at most 1 mm, and a predetermined accurate value of this depth is critical for the subsequent use of the cuvette, the provision of embossments is preferred. Advantageously these embossments are arranged in a predetermined pattern.

When a very precise cavity depth of the cuvette is required it is important that the depression(s) and the joining of the sheets are performed in such a way that the cavity depth is independent of subsequent steps in the cuvette production method. According to the invention it is preferable that the depression(s) is (are) performed by vacuum forming technique using a positive die. It is also preferable that the inner surface of the sheets are provided with embossments prior to the adhesion of the sheets. The embossment is used to guide optional superfluous adhesive to areas between the embossment. It is also preferable to use an adhesive, which does not modify the surface of the sheet, such as an adhesive, cured by UV-light.

The microcuvette or microdevice according to the invention is especially useful for making optical analyses on fluids such as whole blood, serum, plasma, urine, spinal and interstitial fluids. After the sampling procedure when e.g. blood is sucked from the finger tip of a patient into the microcuvette by capillary action, the microcuvette is inserted into a separate spectrophotometer calibrated for the desired type of analysis. The use of a separate spectrophotometer is a major difference between the present invention and the invention disclosed in EP 172 540, the object of which is to provide an analysis instrument in which the reaction chamber, which is also called a cuvette, is produced within the analysis instrument. This arrangement is perceived to provide an economic advantage in that it eliminates the cost of the prior formation of the chamber. When the reaction chamber or cuvette leaves the instrument, the reaction as well as the analysis are completed and the cuvette is disposed of. The EP patent thus concerns cuvettes which can only be used in connection with the analysis instrument, in which the cuvette is formed, and not for analysis in different other analysis instruments. Furthermore, the principle for the production of cavities in these known cuvettes is based on the deformation of a plastic material into close contact with a mould cavity by using a jet of hot air which is quite contrary to the principle according to the present invention which uses vacuum forming in order to obtain the cavity. Another important difference is the type of inlet opening for reagents and samples as well as the methods of introducing the samples and reagents.

The invention is further illustrated by but not limited to the example disclosed in FIG. 1.

A first sheet or lid sheet and a second sheet or base sheet of PVC are provided separately. Eight venting holes are provided in the lid sheet and a reagent, e.g. an enzyme is ink printed next to the holes. Eight cavities are vacuum-formed simultaneously in the base sheet. The depths of the cavities were selected to be 140 $\mu$m but other cavity depths may be used. The sheets were dried in tunnels and joined together by using UV sensitive glue (Locktite 3106). Cuvettes were subsequently cut from the multiple cuvette sheet, by cutting or punching and packed.

What is claimed is:

1. A method for continuous production of disposable capillary plastic microcuvettes comprising the steps of:

providing a first sheet and a second sheet;

providing a plurality of depressions having a predetermined depth at a predetermined place in at least one of the sheets;

placing the sheets in a superimposed relationship;

joining the first sheet and the second sheet for obtaining a body member including at least one capillary cavity having a predetermined volume, the inner walls of the cavity being defined by at least one of said plurality of depressions and a predetermined area of the opposite sheet, the distance between these inner walls defining a predetermined optical path length;

cutting out or punching a plurality of microcuvettes from the body member, each microcuvette including at least one cavity and having a predetermined size and configuration, such that at least one cavity of each microcuvette is communicating with the exterior atmosphere of the microcuvette through a capillary sample inlet opening;

wherein said plurality of depressions correspond in number at least to the number of said plurality of microcuvettes cut or punched from the body member.

2. The method according to claim 1 for continuous production, wherein at least one sheet is provided in the form of a continuous plastic film.

3. The method according to claim 1, wherein the at least one depression is provided by vacuum forming.

4. The method according to claim 1, wherein a plurality of depressions are arranged in at least one sheet.

5. The method according to claim 1, wherein embossments are provided in a predetermined pattern around the depressions.

6. The method according to claim 1, wherein venting holes are provided in one sheet.

7. The method according to claim 1, comprising providing an UV sensitive adhesive on those surfaces of the sheets which are to be joined.

8. The method according to claim 7, wherein the adhesive is applied by screen printing.

9. The method according to claim 1, wherein the additive and/or reagent is liquid and provided by printing.

10. The method according to claim 1, wherein the additive and/or reagent is dried before the sheets are placed in a superimposed relationship.

11. The method according to claim 10, wherein the predetermined distance between the walls of the capillary cavity defining the optical path is less than 1 mm.

12. The method according to claim 1, further comprising introducing at least one additive and/or reagent into at least one depression.

* * * * *